United States Patent [19]

Heyward et al.

[11] Patent Number: 4,487,851

[45] Date of Patent: Dec. 11, 1984

[54] CATALYST COMPOSITION FOR CONVERSION OF SYNTHESIS GAS TO HYDROCARBONS

[75] Inventors: Malcolm P. Heyward, Frimley; Dennis Young, Staines, both of England

[73] Assignee: British Petroleum Company, p.l.c., London, England

[21] Appl. No.: 474,577

[22] PCT Filed: Jul. 15, 1982

[86] PCT No.: PCT/GB82/00210

§ 371 Date: Feb. 22, 1983

§ 102(e) Date: Feb. 22, 1983

[87] PCT Pub. No.: WO83/00326

PCT Pub. Date: Feb. 3, 1983

[30] Foreign Application Priority Data

Jul. 17, 1981 [GB] United Kingdom ............... 8122174
Nov. 19, 1981 [GB] United Kingdom ............... 8134856

[51] Int. Cl.$^3$ .................................. C07L 1/04
[52] U.S. Cl. ........................... 518/728; 518/713; 518/714; 518/715; 518/716; 518/721
[58] Field of Search ............... 518/713, 714, 715, 716, 518/721, 728

[56] References Cited

U.S. PATENT DOCUMENTS

| | | | |
|---|---|---|---|
| 3,709,979 | 1/1973 | Chu | 423/328 |
| 4,086,262 | 4/1978 | Chang et al. | |
| 4,208,305 | 6/1980 | Kouwenhoven et al. | 518/714 |
| 4,331,774 | 5/1982 | Boersma et al. | 518/728 |
| 4,338,089 | 7/1982 | Schaper et al. | 518/728 |

FOREIGN PATENT DOCUMENTS 1495794 12/1977 United Kingdom ............... 518/715
2,089,368 6/1982 United Kingdom .

*Primary Examiner*—Howard T. Mars
*Attorney, Agent, or Firm*—Brooks, Haidt, Haffner & Delahunty

[57] ABSTRACT

Process for conversion of synthesis gas to hydrocarbons in general and to aromatics rich gasoline in particular by contacting the gas with a catalyst composition comprising gallium oxide and/or indium oxide and at least one additional oxide of a metal from Group IB-VIIB or VIII of the Periodic Table. Cerium, thorium, and uranium are the preferred additional metals. The catalyst composition may optionally contain a further component e.g. a zeolite which in some cases can also act as a support. The present process (i) results in a low make of $C_1$ to $C_2$ hydrocarbons, (ii) is capable of using synthesis gas which has a low $H_2$:CO ratio, and (iii) gives a higher conversion of CO than achieved hitherto under similar conditions.

15 Claims, No Drawings

CATALYST COMPOSITION FOR CONVERSION OF SYNTHESIS GAS TO HYDROCARBONS

The present invention relates to a novel catalyst composition for the conversion of synthesis gas to hydrocarbons.

Gallium containing catalyst compositions and the use thereof as hydrocarbon conversion catalysts are well known. These are claimed and described for example in our British Patent Specification Nos. 1496379, 1507549, 1507778, 1537780 and 1533169, and in our published European Patent Application Nos. 0024147 and 0024930. Amongst the various hydrocarbon conversion processes disclosed in these publications are dehydrogenation, dimerisation, isomerisation, cyclisation and aromatisation. It is also known from British Patent Specification No. 1495794 that aluminosilicates when used in conjunction with a metal compound of appropriate activity can convert synthesis gas to higher molecular weight hydrocarbons especially if used together with an alumina binder.

It has now been found that for the conversion of synthesis gas to hydrocarbons using a specific combination of metal compounds as catalysts shows improved activity.

Accordingly, the present invention is a process for converting synthesis gas to hydrocarbons by contacting said synthesis gas with a catalyst composition, characterised in that the catalyst composition comprises an oxide of at least one metal selected from gallium and indium, and contains an oxide of at least one additional metal selected from Group VIII and the B group elements of Groups I-VII including the Lanthanides and Actinides of the Periodic Table of Elements.

The Periodic Table of Elements referred to herein is the Table appearing on pages 448 and 449 of the 44th Edition of the "Handbook of Chemistry and Physics", edited by Hodgman, C. D. and published by The Chemical Rubber Publishing Co., Ohio, USA (1963).

The additional oxide is preferably that of at least one metal selected from copper, zinc, scandium, yttrium, lanthanum, titanium, zirconium, hafnium, chromium, molybdenum, tungsten, manganese, rhenium, iron, ruthenium, cobalt, rhodium, iridium, nickel, palladium, platinum, cerium, terbium, uranium and thorium. Oxides of thorium, cerium and uranium are most preferred.

The catalyst compositions used in the present process are suitably prepared by mixing the respective compounds; for instance, by mixing a suspension of the respective compounds, eg the oxides, in water and evaporating the mixture to form a cake. The cake may thereafter be filtered, washed and dried, and the dried cake crushed and calcined at elevated temperature to produce the desired catalyst composition. The calcination is suitably carried out in an oxidising atmosphere, eg air.

The respective amounts of gallium and/or indium and the additional metal components in the catalyst composition may vary over a wide range depending upon the end use of the catalyst. Thus, in the catalyst compositions now used, the oxides of gallium and/or indium are suitably present in an amount of between 1-75% by weight preferably between 5 and 50% by weight; correspondingly, the additional metal oxide is suitably present in an amount of between 25 and 99% by weight preferably between 50 and 95% by weight.

The catalyst compositions used in the present invention may contain in addition to the metal compounds a further component which in some cases can also act as support. This further component is suitably a crystalline silicate, preferably a crystalline aluminosilicate having a high silica to alumina ratio ie greater than 5:1. Specific examples of such aluminosilicates include the MFI type zeolites eg ZSM-5; the MEL type zeolites eg ZSM-11; ZSM-12; ZSM-23; ZSM-35; ZSM-38; zeolite-$\beta$ and the MOR type zeolites (MFI, MEL and MOR are examples of zeolite structure types nomenclature recommended by IUPAC in "Chemical Nomenclature, and Formulation of Compositions of Synthetic and Natural Zeolites," IUPAC Yellow Booklet, 1978; See also "Atlas of Zeolite Structure Types" by W M Meier and D H Olsen, International Zeolite Association, 1978). Thus in the catalyst composition now used the combined amount by weight of the gallium and/or indium oxides and the additional metal oxide is suitably between 1 and 100%, preferably between 5 and 100%; and the amount by weight of the further component may be suitably between 0 and 99%, preferably between 0 and 95%.

The catalyst compositions used in the present invention may be pelletised or extruded together with a binder. Such binders will be known to those skilled in the art. Examples of such binders include silica and alumina.

In the catalyst compositions now used, the choice of the additional metal oxide and the further component will depend upon the end product desired. For example a composition containing gallium oxide and/or indium oxide with thorium oxide is best suited for producing $C_3$ and $C_4$ hydrocarbons from synthesis gas. On the other hand, if the gallium and/or indium oxide mixed with thorium oxide is supported on or mixed with a zeolite with a high silica to alumina ratio, the principal product of the synthesis gas conversion is a high quality gasoline rich in aromatics. If, however, the silica to alumina ratio of the support is very high as typified by silicalite then a product rich in olefins is formed.

The reaction producing high quality gasoline is also favoured by the use of oxides of gallium and/or indium which have a high surface area. For example in the case of gallium oxide, the surface area is preferably greater than 40 m$^2$/g. An oxide of gallium, known as $\beta$-gallia and defined in "The Chemistry of Gallium" by Sheka, I. A. et al and published by Elsevier, Amsterdam (1966) is most preferred.

The nature of the products is also to some extent dependent upon the reaction conditions such as temperature and pressure. For example, a synthesis gas having a hydrogen to carbon monoxide ratio between 0.2:1 and 6:1 may be converted to hydrocarbons by passing over the catalyst of the present invention at a temperature suitably between 200° and 800° C., preferably between 300° and 600° C. The reaction pressure may be between 1 and 1000 bar, preferably between 30 and 300 bar. The products of this reaction will be rich in hydrocarbons, especially $C_4$ paraffins if gallium and/or indium oxide and thorium oxide are the only components present in the catalyst composition. Combination of these components with a silica matrix appears to favour olefins, especially isobutene. In both cases alcohols, especially methanol, can be formed in particular at low conversions. However, from the same feedstock, under the same reaction conditions using the same catalyst composition (with or without the silica) but now combined with a crystalline aluminosilicate, the product is principally a high quality gasoline rich in $C_6$-$C_{10}$ aromatics. If, however, the silica to alumina ratio of the support is very high as typified by silicalite then a product rich in olefins is formed.

In these cases, there is a low make of $C_1$ and $C_2$ hydrocarbons.

The catalysts and process of the present invention are further illustrated with reference to the following Examples and Comparative tests.

EXAMPLES

A. Catalyst Preparation (i) A gallium oxide suspension was prepared by slurrying 1.8 g of gallium oxide (BET surface area 57 m$^2$/g, mainly $\beta$-phase) oxide in 50 ml of hot (80°–100° C.) distilled water.

A solution containing thorium nitrate (24 g) dissolved in 200 ml of distilled water was heated to boiling. Another solution containing anhydrous $Na_2CO_3$ (9.5 g) in 200 ml distilled water was also heated to boiling and then added to the thorium nitrate solution to precipitate thorium oxide. This precipitate was filtered while still hot and washed with 15×40 ml boiling distilled water. The precipitate was resuspended in 150 ml of hot (80°–100° C.) distilled water and the suspension of gallium oxide added to it. The oxides of thorium and gallium were thoroughly stirred and the water subsequently evaporated without stirring in an oven at 110° C. for 20 hours to form a cake of the mixed oxides of gallium and thorium. The cake was then crushed and sieved to a particle size of 8–30 mesh (BSS) and calcined in a slow stream of air at 300° C. for 4 hours.

(ii) A mixture of the oxides of gallium and thorium was prepared as described in A(i) above (with the exception of the final calcination stage), then crushed and sieved to a particle size smaller than 100 mesh (BSS). 5 g of the resultant powder were mixed thoroughly with 5 g of a crystalline aluminosilicate in its H-form prepared according to the method described in Example 1 of our published European Patent Application No. 0024930, characterised by having a silica to alumina ratio of at least 5:1, and a particle size smaller than 100 mesh (BSS). This mixture was bound with 15 g Ludox AS40 colloidal silica (40 wt% in water) (Ludox is a Registered Trade Mark). After drying for 20 hours at 110° C. the bound catalyst was crushed and sieved to a particle size of 8–30 mesh (BSS) before calcining in a slow stream of air at 300° C. for 4 hours.

(iii) A bound gallium oxide and thorium oxide catalyst mixed with a crystalline aluminosilicate was prepared as in A(ii) above, except that the gallium oxide suspension contained 2.6 g of gallium oxide instead of 1.8 g.

(iv) 1.8 g $In_2O_3$ (ex BDH, General Purpose Reagent) was slurried in 200 ml of distilled water in which had been dissolved 24 g thorium nitrate. This slurry was heated to boiling. Another solution containing anhydrous $Na_2CO_3$ (9.5 g) in 200 ml distilled water was also heated to boiling and then added to the slurry to precipitate thorium oxide onto the indium oxide. The combined solids were filtered while still hot and washed with 15×40 ml distilled water before drying at 110° C. for 20 hours. The mixed oxides were crushed and sieved to a particle size smaller than 100 mesh (BSS). 5 g of the resultant powder were mixed thoroughly with 5 g of a crystalline aluminosilicate in its H-form prepared according to the method described in Example 1 of our published European Patent Application No. 0024930, characterised by having a silica to alumina ratio of at least 5:1, and a particle size smaller than 100 mesh (BSS). This mixture was bound with 15 g Ludox AS40 colloidal silica (40% wt in water) (Ludox is a Registered Trade Mark). After drying for 20 hours at 110° C. the bound catalyst was crushed and sieved to a particle size of 8–30 mesh (BSS) before calcining in air at 500° C. for 16 hours.

(v) A mixture of the oxides of gallium and thorium was prepared as described in A(iv), substituting $Ga_2O_3$ (BET surface area 57 m$^2$/g, mainly $\beta$-phase) for $In_2O_3$. After crushing and sieving the mixed oxides to a particle size smaller than 100 mesh (BSS), 5 g of the resultant powder were mixed thoroughly with 5 g of silicalite in its H-form, also having a particle size smaller than 100 mesh (BSS). This mixture was bound with 15 g Ludox AS40 colloidal silica. After drying for 20 hours at 110° C. the bound catalyst was crushed and sieved to a particle size of 8–30 mesh (BSS) before calcining in air at 300° C. for 4 hours.

(vi) A mixture of the oxides of gallium and thorium was prepared as described in A(iv), substituting $Ga_2O_3$ (BET surface area 97 m$^2$/g, mainly gamma-phase) for $In_2O_3$. After crushing and sieving the mixed oxides to a particle size smaller than 100 mesh (BSS), 10 g of the resultant powder were bound with 10 g Ludox AS40 colloidal silica (40 wt% in water) (Ludox is a registered trademark). After drying for 20 hours at 110° C. the bound catalyst was crushed and sieved to a particle size of 8–30 mesh (BSS) before calcining in a slow stream of air at 300° C. for 4 hours.

(vii) Cerous nitrate was calcined at 560° C. for 16 hours. 13.67 g of the resultant ceria was added to 1.86 g gallia (BET surface area 57 m$^2$/g, mainly $\beta$-phase) and the two components thoroughly mixed then crushed to a particle size smaller than 100 mesh (BSS).

5 g of mixed oxides was mixed thoroughly with 5 g of a crystalline aluminosilicate in its H-form prepared according to the method described in Example 1 of our published European Patent Application No. 0024930 characterised by having a silica to alumina ratio of at least 5:1, and with a particle size smaller than 100 mesh (BSS). This mixture was bound with 15 g Ludox AS40 colloidal silica. After drying for 20 hours at 110° C. the bound catalyst was crushed and sieved to a particle size of 8–30 mesh (BSS) before calcining in a slow stream of air at 300° C. for 4 hours.

(viii) Uranyl nitrate was calcined at 560° C. for 16 hours. 5 g of the resultant uranium trioxide was added to 0.67 gallia (BET surface area 57 m$^2$/g, mainly $\beta$-phase) and the two components thoroughly mixed then crushed to a particle size smaller than 100 mesh (BSS).

5 g of mixed oxides was mixed thoroughly with 5 g of a crystalline aluminosilicate in its H-form prepared according to the method described in Example 1 of our published European Patent Application No. 0024930 characterised by having a silica to alumina ratio of at least 5:1, and with particle size smaller than 100 mesh (BSS). This mixture was bound with 15 g Ludox AS40 colloidal silica. After drying for 20 hours at 110° C. the bound catalyst was crushed and sieved to a particle size of 8–30 mesh (BSS) before calcining in a slow stream of air at 300° C. for 4 hours.

Comparative tests 1 and 8 below do not constitute Examples of the present invention and are included only for purposes of comparison.

COMPARATIVE TEST 1

A mixture of thorium oxide and alumina was prepared according to the method of Pichler and Ziesecke, as described in "The Isosynthesis", US Bureau of Mines Bulletin, 488, (1950). The material so obtained was crushed to a particle size of 8–30 mesh (BSS).

COMPARATIVE TEST 2

5 g of the catalyst prepared in Comparative Test 1 above was crushed and sieved to a particle size smaller than 100 mesh (BSS), impregnated with potassium acetate and mixed thoroughly with 5 g of a crystalline aluminosilicate in its H-form prepared according to the method described in Example 1 of our published European Patent Application No. 0024930 characterised by having a silica to alumina ratio of at least 5:1, also with a particle size of smaller than 100 mesh (BSS). This mixture was bound with 15 g Ludox AS40 colloidal silica. After drying for 20 hours at 110° C. the bound catalyst was crushed and sieved to a particle size of 8–30 mesh (BSS) before calcining in a slow stream of air at 300° C. for 4 hours.

COMPARATIVE TEST 3

A mixture of thorium oxide and alumina was prepared as in Comparative Test 1 above except that it was crushed and sieved to a particle size smaller than 100 mesh (BSS). 5 g of mixed oxides was mixed thoroughly with 5 g of a crystalline aluminosilicate in its H-form prepared according to the method described in Example 1 of our published European Patent Application No. 0024930 characterised by having a silica to alumina ratio of at least 5:1, and with a particle size smaller than 100 mesh (BSS). This mixture was bound with 15 g Ludox AS40 colloidal silica. After drying for 20 hours at 110° C. the bound catalyst was crushed and sieved to a particle size of 8–30 mesh (BSS) before calcining in a slow stream of air at 300° C. for 4 hours.

COMPARATIVE TEST 4

A mixture of thorium oxide and alumina was prepared as in Comparative Test 3 above. 5 g of this material was mixed thoroughly with 5 g of silicalite in its H-form, also having a particle size smaller than 100 mesh (BSS). This mixture was bound with 15 g Ludox AS40 colloidal silica. After drying for 20 hours at 110° C. the bound catalyst was crushed and sieved to a particle size of 8–30 mesh before calcining in air at 300° C. for 4 hours.

B. EXAMPLES 1–8 AND COMPARATIVE TESTS 5 TO 8

Hydrocarbon conversion reaction using the catalysts of A(i)–A(viii) and Tests 1–4

Examples 1–3 and Comparative Tests 5 and 6

10 ml each of the catalysts from Catalyst Preparations A(i)–A(iii) above and Comparative Tests 1 and 2 were charged in turn to a fixed bed reactor. The reactor was pressurised to 50 bar under flowing $N_2$ (5 L/hr) and the temperature raised to 150° C. before stopping $N_2$ flow and commencing a flow of 1:1 $CO/H_2$ at a rate of 5 L/hr, measured at STP, while the temperature was raised at about 200° C./hr to the reaction temperature as shown in the Table below. The flow rate was subsequently adjusted to give the space velocities indicated in the Table below. Heated off-gases were analysed by online gas chromatography and, where appropriate, they were passed through a cardice/acetone cold trap and the liquid formed was then analysed.

The results of passing 1:1 $CO/H_2$ over the various catalysts are also shown in the Table 1 below.

TABLE 1

| Run | Example 1 | Example 2 | Example 3 | Test 5 | Test 6 |
|---|---|---|---|---|---|
| Catalyst from | Prep. A(i) | Prep. A(ii) | Prep. A(iii) | Test 1 | Test 2 |
| Temperature °C. | 325 | 450 | 400 | 450 | 530 |
| VHSV (1) | 2000 | 800 | 905 | 500 | 960 |
| HOS | 8.5 | 4 | 8 | 4 | 7.5 |
| % conversion of CO | 9 | 48 | 55 | 17 | 22 |
| Selectivity (2) | 59 | 51 | 54 | 52 | 55 |
| H/C, WT % | | | | | |
| $C_1$ | 27.3 | 6.5 | 5.7 | 31.4 | 32.2 |
| $C_2$ | | 5.3 | 5.5 | 20.8 | 15.0 |
| $C_3$ | 2.6 | 17.9 | 26.9 | 9.9 | 14.8 |
| $C_4$ | 36.9 | 21.6 | 14.3 | 12.9 | 7.8 |
| $C_4=$ | 8.4 | | | | 12.0 |
| Total $C_5+$ | 24.8 | 48.7 | 47.6 | 13.1 | 30.2 |
| Aromatics in $C_5+$ (%) | 39.9 | 61.4 | 85.5 | 42.7 | 88.1 |

(1) VHSV based on total catalyst volume and gas at STP
(2) Selectivity = $\frac{100 \times CO\ converted\ to\ hydrocarbon}{Total\ CO\ converted}$ It can be seen from the above that the results from Example 1 are superior to those of Test 5 which were both carried out in the absence of a zeolite. Moreover, Test 5 was carried out at a higher temperature (450° C.) and a lower space velocity than Example 1. Similarly, Examples 2 and 3 are superior to those in Test 6 although in this instance a zeolite was used as a catalyst component in each case.

Examples 4 and 5

10 ml of each catalyst from catalyst Preparations A(iv) and A(v) above were charged in turn to a fixed bed reactor. The reactor was pressurised to 50 bar under 1:1 $CO/H_2$, flowing at a rate of about 20 L/hr, measured at STP. The temperature was raised at the rate of about 200 degrees C./hr to the reaction temperatures as shown in Table 2 below. Heated off gases were analysed by online gas chromatography. The results are shown in Table 2 below.

Comparative Tests 7 and 8

Comparative Tests 7 and 8 were conducted in a similar manner to Examples 4 and 5 utilising in turn each of the catalyst preparations described in the Comparative Tests 3 and 4 above. The results are shown in Table 2 below.

TABLE 2

| Run Catalyst from | Example 4 Prep A(iv) | Test 7 Test 3 | Example 5 Prep A(v) | Test 8 Test 4 |
|---|---|---|---|---|
| Temperature °C. | 441 | 465 | 465 | 450 |
| VHSV (1) | 2330 | 3050 | 2120 | 1000 |
| HOS | 0.5 | 0.5 | 0.5 | 1.5 |
| % conversion of CO | 38 | 10 | 13.5 | 7.8 |
| Selectivity (2) | 61 | 52 | 51 | 53 |
| H/C, wt % | | | | |
| $C_1 + C_2$ | 28.3 | 49.2 | 42 (3) | 80.3 |
| $C_3$ | 12 | 17.5 | 13.3 (4) | 7.9 |
| $C_4$ | 18.7 | 4.6 | 22.5 (5) | 3.8 |
| Total $C_5+$ | 41.0 | 28.6 | 22.3 | 7.7 |
| Aromatics in | 61.7 | 94.0 | — | — |

TABLE 2-continued

| Run<br>Catalyst from | Example 4<br>Prep A(iv) | Test 7<br>Test 3 | Example 5<br>Prep A(v) | Test 8<br>Test 4 |
| --- | --- | --- | --- | --- |
| $C_5^+$ (%) | | | | |

Notes
(1) Gas flow rate measured at STP
(2) Selectivity = $100 \times \frac{\text{CO converted to hydrocarbons}}{\text{Total CO converted}}$
(3) Molar fraction ethylene in $C_2$ = 0.30
(4) Molar fraction propylene in $C_3$ = 0.45
(5) Molar fraction butene in $C_4$ = 0.63

Example 6

Example 6 was conducted in a similar manner to Examples 4 and 5 above utilising the catalyst preparation described in A(vi). The results are shown in Table 3 below.

TABLE 3

| Run<br>Catalyst from | Example 6<br>Prep A(vi) |
| --- | --- |
| Temperature °C. | 375 |
| VHSV (1) | 4160 |
| % Conversion of CO (2) | 6.7 |
| H/C, wt % | |
| $C_1$ | 11.2 |
| $C_2 + C_2^=$ | 23.5 |
| $C_3$ | 2.1 |
| $C_3^=$ | 6.8 |
| $C_4$ | 6.1 |
| $C_4^=$ (3) | 48.2 |
| $C_5^+$ | 1.9 |

(1) Gas flow rate measured at STP
(2) Methanol, hydrocarbon (H/C) and $CO_2$ produced,
$\frac{100 \text{ H/C}}{\text{MeOH} + \text{H/C}} = 45$ wt %
(3) The great majority was isobutene.

Examples 7 and 8

Examples 7 and 8 were conducted in a similar manner to Examples 1 to 3 above utilising in turn each of the catalyst preparations described in A(vii) and A(viii). The results are shown in Table 4 below.

TABLE 4

| Run<br>Catalyst from | Example 7<br>A(vii) | Example 8<br>A(viii) |
| --- | --- | --- |
| Temperature °C. | 380 | 414 |
| VHSV (1) | 2250 | 2000 |
| HOS | 3.7 | 3.5 |
| % Conversion of CO | 29.0 | 13.5 |
| Selectivity (2) | 58.0 | 57.0 |
| H/C, wt % | | |
| $C_1 + C_2$ | 46.3 | 38.3 |
| $C_3$ | 23.9 | 22.4 |
| $C_4$ | 9.7 | 12.7 |
| Total $C_5^+$ | 20.1 | 26.5 |
| Aromatics in $C_5^+$ (%) | 77.6 | 72.8 |

(1) Gas flow rate measured at STP
(2) Selectivity = $\frac{100 \times \text{CO converted to hydrocarbon}}{\text{Total CO converted}}$ From these results it is clear that the catalysts of the present invention show several advantages over prior art processes. Taking the example of synthesis gas conversion:

(a) there is a low make of $C_1$ and $C_2$ hydrocarbons;
(b) carbon dioxide is a major oxygenated product and hence there is a built-in water shift reaction; therefore the process is capable of using synthesis gases which have low hydrogen to carbon monoxide ratios such as eg those derived from coal;
(c) the process gives a higher conversion of carbon monoxide than achieved hitherto under similar conditions using analogous catalysts eg $Al_2O_3$ rather than $Ga_2O_3$; and
(d) a choice of end-products can be produced from the same feedstock by varying the catalyst and this makes the catalyst versatile.

We claim:

1. In a process for converting synthesis gas to hydrocarbons by contacting said synthesis gas with a catalyst composition, the improvement which comprises that the catalyst composition comprises an oxide of at least one metal selected from gallium and indium, and contains an oxide of at least one additional metal selected from Group VIII and the B group elements of Group I-VII including the Lanthanides and Actinides of the Periodic Table of Elements, and wherein the catalyst composition optimally contains a further component capable of acting as support.

2. A process according to claim 1 wherein the additional oxide is that of at least one metal selected from copper, zinc, scandium, yttrium, lanthanum, titanium, zirconium, hafnium, chromium, molybdenum, tungsten, manganese, rhenium, iron, ruthenium, cobalt, rhodium, iridium, nickel, palladium, platinum, cerium, terbium, uranium and thorium.

3. A process according to claim 1 wherein the further component is a crystalline silicate or a crystalline aluminosilicate.

4. A process according to claim 4 wherein the crystalline aluminosilicate has a silica to alumina ratio greater than 5:1.

5. A process according to claim 1, wherein the catalyst composition used is pelletised or extruded together with a binder.

6. In a process for the conversion of synthesis gas to hydrocarbons having 3 to 4 carbon atoms by bringing the synthesis gas into contact with a catalyst composition the improvement which comprises that the catalyst composition comprises an oxide of at least one metal selected from gallium and indium, and at least one additional oxide of a metal selected from cerium, thorium and uranium.

7. In a process for conversion of synthesis gas to a gasoline rich in aromatics by bringing the synthesis gas into contact with a catalyst composition, the improvement which comprises that the catalyst composition comprises an oxide of at least one metal selected from gallium and indium, at least one additional oxide of a metal selected from cerium, thorium and uranium, and an aluminosilicate component which has a silica to alumina molar ratio greater than 5:1.

8. A process according to claim 7 wherein the oxide of gallium and/or indium in the catalyst composition has a surface area greater than 40 $m^2$/g.

9. A process according to claim 6 or 7, wherein the synthesis gas is brought into contact with the catalyst at a temperature between 200° and 800° C. and a pressure between 1 and 1000 bars.

10. A process according to claim 1, 6 or 7, wherein said oxide of at least one metal selected from gallium and indium is present in an amount of between 1 to 75% by weight, and wherein said oxide of at least one additional metal is present in an amount of between 25 to 99% by weight.

11. A process according to claim 10, wherein said oxide of at least one metal selected from gallium and indium is present in an amount of between 5 to 50% by weight, and wherein said oxide of at least one additional metal is present in an amount of between 50 to 95% by weight.

12. A process according to claim 1, 6 or 8, wherein said metal oxide is indium oxide.

13. A process according to claim 1 or 6, wherein the oxide of gallium and/or indium in the catalyst composition has a surface area greater than 40 $m^2/g$.

14. A process according to claim 1, 6 or 7, wherein the oxide of gallium in the catalyst composition has a surface area greater than 40 $m^2/g$ up to 97 $m^2/g$.

15. A process according to claim 1, 6 or 7, wherein the oxide of gallium in the catalyst composition has a surface area of from 57 $m^2/g$ to 97 $m^2/g$.

* * * * *

UNITED STATES PATENT AND TRADEMARK OFFICE
CERTIFICATE OF CORRECTION

PATENT NO. : 4,487,851

DATED : December 11, 1984

INVENTOR(S) : MALCOLM P. HEYWARD et al

It is certified that error appears in the above-identified patent and that said Letters Patent is hereby corrected as shown below:

Col. 4, line 51, "to 0.67 gallia..." should read --"to 0.67g gallia--

Col. 8, claim 4, line 30, "according to claim 4" should read --according to claim 3--

Col. 9, claim 12, line 6, "according to claim 1, 6 or 8" should read --according to claim 1, 6 or 7--

Signed and Sealed this

Thirtieth Day of April 1985

[SEAL]

Attest:

DONALD J. QUIGG

Attesting Officer     Acting Commissioner of Patents and Trademarks